(12) United States Patent
Chen et al.

(10) Patent No.: US 7,034,941 B2
(45) Date of Patent: Apr. 25, 2006

(54) COLOR DETECTION USING SPECTROSCOPIC IMAGING AND PROCESSING IN RANDOM ARRAY OF MICROSPHERES

(75) Inventors: Samuel Chen, Penfield, NY (US); Anthony E. Taddei, Hilton, NY (US); Joaquin Calcines, West Henrietta, NY (US); Krishnan Chari, Fairport, NY (US); Martin C. Kaplan, Rochester, NY (US); Douglas L. Vizard, Durham, CT (US)

(73) Assignee: Eastman Kodak Company, Rochester, NY (US)

( * ) Notice: Subject to any disclaimer, the term of this patent is extended or adjusted under 35 U.S.C. 154(b) by 374 days.

(21) Appl. No.: 10/607,146

(22) Filed: Jun. 26, 2003

(65) Prior Publication Data

US 2004/0265905 A1   Dec. 30, 2004

(51) Int. Cl.
*G01J 3/46* (2006.01)
(52) U.S. Cl. .................................... 356/402
(58) Field of Classification Search ............. 356/336, 356/337, 338; 435/6
See application file for complete search history.

(56) References Cited

U.S. PATENT DOCUMENTS

| | | | |
|---|---|---|---|
| 5,412,087 A | 5/1995 | McGall et al. | |
| 5,422,730 A * | 6/1995 | Barlow et al. | 356/417 |
| 5,489,678 A | 2/1996 | Fodor et al. | |
| 5,866,911 A * | 2/1999 | Baer | 250/458.1 |
| 5,981,180 A | 11/1999 | Chandler et al. | |
| 6,023,540 A | 2/2000 | Walt et al. | |
| 6,916,620 B1 * | 7/2005 | Qiao et al. | 435/6 |
| 6,942,987 B1 * | 9/2005 | Auld | 435/15 |
| 6,958,470 B1 * | 10/2005 | Hoffmann | 250/234 |
| 2003/0143542 A1 * | 7/2003 | Qiao et al. | 435/6 |
| 2004/0125441 A1 * | 7/2004 | Wang et al. | 359/385 |
| 2004/0171076 A1 * | 9/2004 | Dejneka et al. | 435/7.1 |

OTHER PUBLICATIONS

Principles of Instrumental Analysis, Fourth Edition, Douglas A. Skoog, James J. Leary-An Introduction to Molecular Ultraviolet/Visible and Near-Infrared Absorption Spectroscopy, pp 123-127.
Understanding The Light Microscope, D.J. Goldstein, 1999, text book, ISBN:0-12-288660-7.
Fundamentals of Light Microscopy and Electronic Imaging, Douglas B. Murphy, 2001, text book, ISNB:0-471-25391-X.

(Continued)

*Primary Examiner*—Gregory J. Toatley, Jr.
*Assistant Examiner*—Ali Allawi
(74) *Attorney, Agent, or Firm*—William F. Noval

(57) ABSTRACT

A method of determining one or more color characteristics of a colored microsphere comprising: providing a microarray of microspheres, including at least one colored microsphere which has a color characteristic; producing a magnified optical image of individual microspheres of the microarray; locating a microsphere in the aperture of a spectrometer to confine the color region of interest of the located microsphere in order to determine one or more color characteristics thereof; and determining one or more color characteristics of the located microsphere by means of the spectrometer.

11 Claims, 3 Drawing Sheets

OTHER PUBLICATIONS

Quantum-dot-tagged microbeads for multiplexed optical coding of biomolecules, Mingyong Han, Xiaohu Gao, Jack Z. Su, Shuming Nie, Nature Biotechnology, vol. 19, pp 631-635, 2001.

Block Copolymer Lithography: Periodic Arrays of ~10 Holes in 1 Square Centimeter, Miri Park, Christopher Harrison, Paul M. Chaikin, Richard A. Register, Douglas H. Adamson, Science, vol. 276, 1997, pp 1401-1404.

Multi-analyte immunoassay, Roger P. Ekins, Journal of Pharmaceutical & Biomedical Analysis, vol. 7, pp 155-168, 1989.

Cross-Reactive Chemical Sensor Arrays, Chem. Rev., 2000, 100, 2595-2626, Keith J. Albert, Nathan S. Lewis, Caroline L. Schauer, Gregory A. Sotzing, Shannon E. Stitzel, Thomas P. Vaid, David R. Walt.

* cited by examiner

COLOR DETECTION USING SPECTROSCOPIC IMAGING AND PROCESSING IN RANDOM ARRAY OF MICROSPHERES

FIELD OF THE INVENTION

This invention relates in general to microarray sensing technology and relates more particularly to color and color level detection in a microarray coated on a substrate that contain no designated sites prior to coating.

BACKGROUND OF THE INVENTION

The concept of multi-analyte sensing using array based sensors (Chem. Rev. 100, 2595–2626, (2000)) has opened up a wide field of technologies in detecting and analyzing specific components (analytes) in a mixture of unknown components. Such technologies benefit industries ranging from the medical, biological, environmental, as well as the consumer sectors. For example, the medical industry depends on analysis for the detection of metabolites, drugs, and glucose; the biological sector needs to detect amino acids, cell components, etc; environmentalists have a need to know the level of gaseous components in water or air; while consumers may want to regularly test for levels of carbon monoxide in houses, airborne allergens, or hardness of water, etc.

The basic principles of microarray assays were already described by the end of the eighties (J. Pharm Biomed Anal 7, 155–168, (1989)). This interest increased dramatically with the development of DNA chip technology. The invention and demonstration in the early 1990s (Science, 251, 767–773, (1991)) that high-density arrays formed by spatially addressable deposition of sensors on a two-dimensional solid support has enhanced and simplified the process of array based sensor technologies. The key to current microarray technology is the placement of receptors at predetermined locations on a microchip in a "spatially addressable" manner. The presence or absence of an analyte is then discerned by monitoring a specific location on a sensor array of receptors. All of these systems require preparing a sensor array with a plurality of receptors at predetermined sites that involve complex and expensive processing steps.

Recent technologies have used various approaches to fabricate microarrays. For example, U.S. Pat. Nos. 5,412,087, and 5,489,678 demonstrate the use of a photolithographic process for making peptide and DNA microarrays. These patents teaches the use of photolabile protecting groups to prepare peptide and DNA microarrays through successive cycles of deprotecting a defined spot on a 1 cm ×1 cm chip by photolithography, then flooding the entire surface with an activated amino acid or DNA base. Repetition of this process allows construction of a peptide or DNA microarray with thousands of arbitrarily different peptides or oligonucleotide sequences at different spots on the array. This method is expensive. Park et al. (Science 276:1401 (1997)) has disclosed a lithographic method for producing array of nanometer-sized holes using polystyrene-polybutadiene copolymer masks in reactive ion etching of silica nitride. This multi-step method is capable of producing arrays of picoliter-sized holes that are typically 20 nanometers in diameter and 20 nanometers deep with a spacing of 40 nanometers. Hole densities of up to $10^{11}$ holes/cm$^2$ are disclosed. The range of sizes and spacings of the holes produced by this method is limited by the size of the copolymer microdomains. Uniformity of hole size and spacing is difficult to maintain with this method due to difficulties in controlling the etching method employed to form the holes.

Because the number of bioactive probes to be placed on a single chip usually runs anywhere from 1000 to 100,000 probes, the spatially addressable method is intrinsically expensive regardless of how the chip is manufactured. An alternative approach is the use of fluorescent dye-incorporated polymeric beads to produce biological multiplexed arrays. U.S. Patent No. 5,981,180 discloses a method of using color-coded beads in conjunction with flow cytometry to perform multiplexed biological assay. Microspheres conjugated with DNA or monoclonal antibody probes on their surfaces were dyed internally with various ratios of two distinct fluorescence dyes. Hundreds of "spectrally addressable" microspheres were allowed to react with a biological sample and the "liquid array" was analyzed by sequentially passing microspheres through a flow cytometry cell to decode sample information. U.S. Patent No. 6,023,540 discloses the use of fiber-optic bundles with pre-etched microwells at distal ends to assemble dye loaded microspheres. The surface of each spectrally addressed microsphere was attached with a unique bioactive agent and thousands of microspheres carrying different bioactive probes combined to form "beads array" on pre-etched microwells of fiber optical bundles. More recently, a novel optically encoded microsphere approach was accomplished by using different sized zinc sulfide-capped cadmium selenide nanocrystals incorporated into microspheres (Nature Biotech. 19, 631–635, (2001)). Given the narrow spectral bandwidth demonstrated by these nanocrystals, this approach significantly expands the spectrally addressable barcoding capacity in microspheres.

Even though the "spectrally addressed microsphere" approach does provide an advantage in terms of its simplicity over the old fashioned "spatially addressable" approach in microarray making, there are still needs in the art to render the manufacture of microarrays less difficult and less expensive.

U.S. patent application Ser. No. 09/942,241 discloses a microarray that is less costly and easier to prepare than those previously disclosed, because the support need not be modified even though the microspheres remain immobilized on the substrate. The disclosed microarray includes microspheres dispersed in a fluid containing a gelling agent or a precursor to a gelling agent, wherein the microspheres are immobilized at random positions on the substrate. The substrate is free of receptacles designed to physically or chemically interact with the microspheres. Disclosed is a unique coding composition and technology to prepare a microarray on a substrate that does not require placement of microspheres at predetermined locations. Various coating methods are taught but there is exemplified machine coating, whereby a support is layered with a fluid coating composition comprising microspheres dispersed in gelatin. Immediately after coating, the support is passed through a chill-set chamber in the coating machine where the gelatin undergoes rapid gelation and the microspheres are immobilized.

Although the disclosure of the latter patent application provides manufacturing advantage over other existing technologies, some limitations need to be overcome. By moving from spatially addressable to randomly positioned microspheres, the information content contained within each bead necessarily must be extracted using a new analysis technology that is not preset-positionally dependent. Furthermore, the colors and color levels need to be accessed uniquely to correlate the tag to the analyte.

It is also known (Nature Biotech. 19, 631–635, (2001)) that the number of different color codes in spectrally addressable microspheres for use in multi-analyte sensing follows the relationship:

Number of optical codes=$(n^m-1)$, where m=color types, and n=color intensity levels For example, 2 colors, with 4 intensity levels each should result in $4^2-1=15$ codes. Hence, in order to sense a large number of analytes, using numerous color types and several color levels, there exists a need for analysis methods to differentiate small changes in color types and color levels, on a micrometer scale.

SUMMARY OF THE INVENTION

According to the present invention, there is provided a solution to these problems of the prior art.

The present invention generally provides a method to analyze and to determine different color types as well as different color levels in individual microspheres loaded with colorants. This method uses a combination of an optical microscope together with a spectrometer such that a magnified image of individual beads is first made, and then the spectral information within each bead is sampled by the spectrometer. Through the proper selection of optic lens to provide the desired magnification, the location of each bead can first be ascertained. Then each bead is positioned such that the aperture of the spectrometer can confine the color region of interest in each bead in order to gather its spectral information.

According to a feature of the present invention, there is provided a method of determining one or more color characteristics of a colored microsphere comprising: providing a microarray of microspheres, at least one of which has a color characteristic; capturing said microarray with an electronic color image sensor assembly having a matrix of pixels; detecting the location of a microsphere within said captured microarray image; and identifying a color characteristic of said detected microsphere using a spectrometer.

ADVANTAGEOUS EFFECT OF THE INVENTION

The invention has the following advantages.

1. A method whereby randomly distributed, color addressable mixed beads in a unique composition can be processed to extract its color component in a simple, cost effective and efficient manner.

2. A method to analyze the color content of microarrays that does not require expensive and complex spatially addressable coated microarrays or spectrally addressable liquid microarrays.

DETAILED DESCRIPTION OF THE INVENTION

Figure 1:
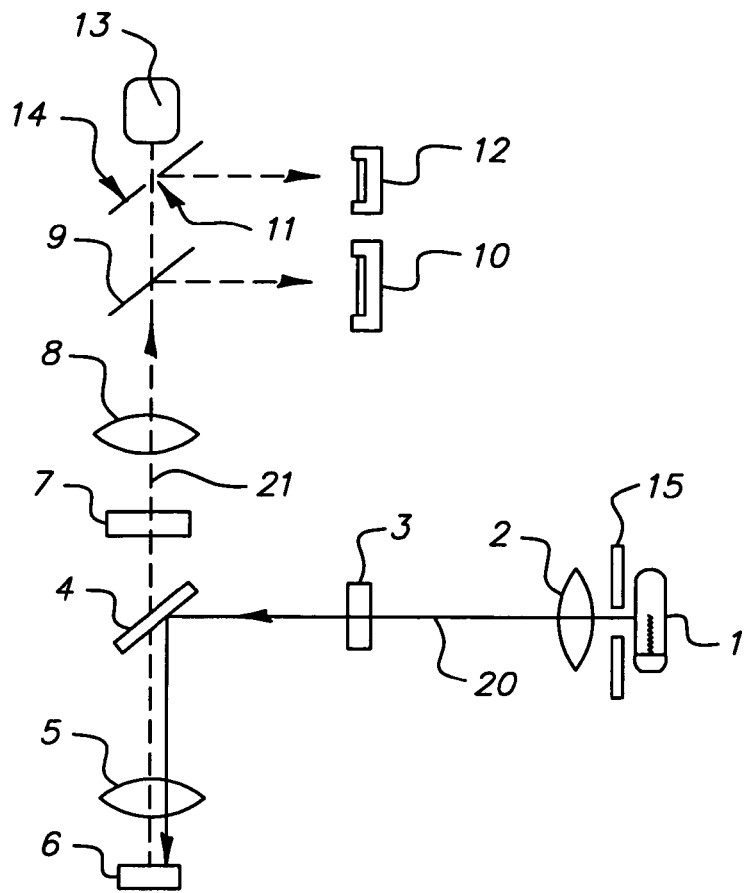
FIG. 1 is a schematic diagram showing the combination of optical microscope and spectrometer components, assembled together for detecting color and color levels in microspheres.

As shown in FIG. 1, color type and color level in microspheres (beads) are analyzed using a hybrid analysis system having three parts: optical microscope, fluorescence microscope, and ultra-violet visible (UV-VIS) micro-spectrometer. This system uses high-intensity light, lenses, mirrors, color filters, apertures and optical detectors to first generate a magnified image of a randomly coated array of microspheres. Such an image not only identifies the location of all the microspheres but it also enlarges the size of the bead to allow for the subsequent color analysis process.

Figure 2:
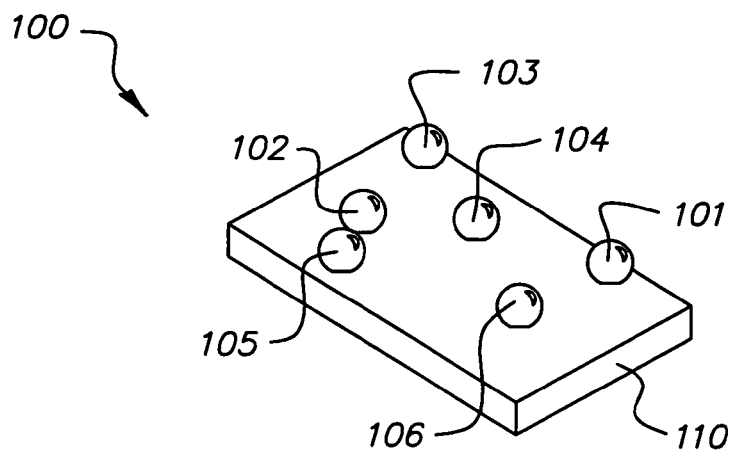
FIG. 2 is a diagrammatic view showing randomly distributed microspheres containing a microsphere without color and microspheres containing a colorant all coated and immobilized on a substrate surface.

FIG. 2 shows a microarray 100 of randomly distributed microspheres including a microsphere 101 containing no color, a microsphere 102 of one color (e.g., yellow) and microspheres 103, 104, 105 and 106 of another color (e.g., magenta) having different color levels or intensities, all coated and immobilized on a substrate 110.

The microarray of beads follows the disclosure in U.S. patent application Ser. No. 09/942,241, in which color addressable mixed beads in a unique composition are randomly distributed on a substrate that has no wells, nor sites to attract the microspheres. Most preferably, the beads are coated on mirrored support. Other preferred supports include transparent and black.

The procedure for obtaining a magnified image starts by focusing excitation light 20 from a light source 1 (e.g. halogen or xenon lamp), through the collector lens assembly 2, onto a dichroic mirror 4, and onto the microarray specimen 6. The reflected or emitted light 21 is then focused by the objective lens 5, and transmitted through the dichroic mirror 4, so that a magnified image of a given field of view can be captured. The removable mirror 9, controls the option of image capture by the digital camera 10, or spectral capture by the micro-spectrometer 13. One such optical microscope is an Olympus BX-30MFSP modular optical system (from Olympus PID Corp, Woodbury, N.Y.), equipped with a Spot RT-Slider Camera (from Diagnostic Instruments, Inc.). Depending on the magnification used, optical microscope imaging can provide the location of hundreds to thousands of beads in a single field of view. The combination of many images can provide the location to tens and hundreds of thousands of bead locations.

For fluorescence microscopy, various color filter cube assemblies (e.g. U-M57, from Olympus PID Corp, Woodbury, N.Y.), each consisting of an exciter filter 3, a dichroic mirror 4, and a barrier filter 7, are inserted into the optical microscope to selectively extract the fluorescence from the analyte tagged on the microsphere. The exciter filter 3 selects the wavelength of the incident light to cause electronic excitation of the analyte species in order to induce fluorescence, which is then channeled through the barrier filter 7, for fluorescence image capture by the digital camera 10. Such an image identifies the location of the analyte tagged on the microsphere, as described in U.S. patent application Ser. No. 09/942,241. Not all microspheres are necessarily tagged with an analyte. The combination of optical microscopy imaging and fluorescence microscopy imaging from the same field can be captured by moving in or out of the color filter assembly, without disturbing the viewing or imaging process. Each image is formed by sequentially taking three color images, each using a red, green or blue color filter, and then merging the three images into a full-color digital image. These pairs of images from the same field of view define the presence of the analyte, as well as the location of the microspheres tagged either with, or without, the analyte. Optical microscopy and fluorescence microscopy methods are broadly described by D. B. Murphy, "Fundamentals of Light Microscopy and Electronic Imaging", Wiley-Liss, Inc. Publishing, (2001); and D. J. Goldstein, "Understanding the Light Microscope. A Computer-aided Introduction", Academic Press, California, (1999).

The location of each bead, or at least each bead that fluoresced, is determined either manually or by image processing software. Manual determination is carried out by a person observing the image, recognizing the location of the bead, and specifying the location, such as by reporting the coordinates or pointing to the bead with a computer pointing device such as a mouse. Alternatively, fully automated (no human intervention) location of each bead may be performed by any of numerous, well known computer image processing algorithms, such as template matching, segmentation, thresholding and region growing, or cluster analysis.

Once the locations of the microspheres are known, each bead can then be analyzed by micro-spectroscopy. For color analysis of individual microspheres in a random array of mixed color microspheres, our use of UV-VIS spectrometry uniquely allows both the color type and colorant concentration to be obtained. This component is comprised of an F-40 light gathering optics setup ( Filmetrics Inc., San Diego) that holds a 45° angled mirror 14 etched with a small aperture 11 as shown in FIG. 1. The image can be reflected from mirror 14 to be captured and displayed on video monitor 12. This feature permits the extraction of spectral information from a specific region, even from a select region less than 10 microns in diameter. The spectral information is then collected on the spectrometer sensor 13 (USB-2000, OceanOptics, Fla.), and processed with the QOIBase32 software (from OceanOptics, Fla.).

Two-dimensional translation of the substrate, containing the microarray 6 in FIG. 1, allows the image of a bead of interest to be positioned within the spectrometer aperture 11. Changes in the magnifying power of the objective lens 5, and the variable zoom lens 8, allow different amounts of the bead area to be confined by the aperture opening. For analysis of colors in these microspheres, in one preferred embodiment, the magnification is such that aperture 11 passes a central portion of the bead image having area less than half the area of the bead image (i.e. for a bead image of diameter D at the aperture, the aperture passes an area of less than $0.5 \times \pi(D/2)^2$). In another preferred embodiment, the aperture passes an area of more than twice the area of the bead image. In another preferred embodiment, the aperture passes between half and twice the area of the bead image.

To obtain the color and color level of colorant in the microsphere, the following procedure is used. First, an adjustment for 0% transmittance is made by collecting the null spectral response intensity value, $I_{background}$, with the light source 1 closed off by a mechanical shutter 15. Then, a maximum transmittance adjustment, $I_{reference}$, is made by selecting a spectral acquisition time with the aperture centered around a microsphere in the coating that contains no colorant. Subsequently, spectral information of the unknown microspheres, $I_{sample}$, is collected, by translating the specimen so that the bead of interest becomes centered at the aperture opening 11. The location of each bead is provided from the optical microscope images, described above. The spectral response data can be processed using the formula below, in which the absorbance A, at each wavelength value is:

$$A = \log((I_{reference} - I_{background})/(I_{sample} - I_{background}))$$

According to Beer's Law, the absorbance, A, can also be expressed as:

$A = \epsilon b\, c$, where $\epsilon$ is the molar absorbativity of the colorant in the bead, b is the length of the bead traversed by the light c is the concentration of the colorant in the bead.

By combining these two relationships, it follows that $$\log((I_{reference} - I_{background})/(I_{sample} - I_{background})) = \epsilon b\, c$$

From this relationship it follows that the measured sample value is proportional to the concentration of the colorant in the microsphere, and the measured absorbance value is a direct indication of the colorant concentration.

Since the measured intensity values is collected over the 300–1000 nm region of the electromagnetic radiation range by the detector, the intensity variation pattern as a function of wavelength is the basis to differentiate the color type of one color-absorbing species from another. By plotting the spectral responses as absorbance vs. wavelength formats, both the color type and colorant concentration of a colorant in a microspheres can be evaluated. The theory and practice of UV-VIS spectroscopy revealed in this disclosure is broadly described by D. A. Skoog and J. J. Leary, in the book "Principles of Analytical Chemistry", Chapter 6 and 7, Saunders College Publishing, (1992).

EXAMPLE 1

This example illustrates the detection of a colored bead and differentiates it from a colorless bead.

A. Preparation of Plain (non-dyed) Beads

A 4.2% aqueous suspension of polystyrene beads prepared by emulsion polymerization and having a mean size of 10 micrometers was obtained from Interfacial Dynamics Corporation, Portland, Oreg.

B. Preparation of Yellow Colored Beads

A suspension of yellow colored beads was prepared by first dissolving 0.006 grams of Dye 1 in 0.02 grams of toluene and 2 grams of acetone. 2.5 grams of the suspension of non-dyed beads from part A was combined with 3 grams of acetone. This mixture was then added rapidly to the solution of Dye 1 in acetone-and toluene while stirring to prepare a suspension of colored beads. The suspension of colored beads was then filtered using a porous cotton filter, poured into a dialysis bag (12,000 to 14,000 molecular weight cut off) and washed with distilled water for one hour. After washing, the suspension of colored beads was filtered again using a porous cotton filter.

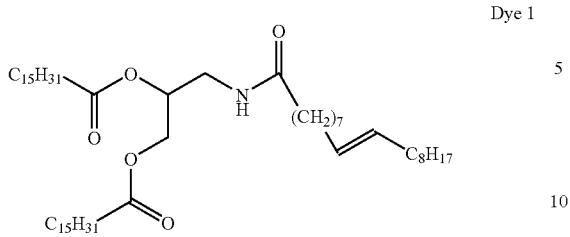

Dye 1

C. Preparation of Coated Array containing Dyed Yellow Beads and Non-Dyed Beads One hundred micro-liters of a 3% aqueous solution of Type IV gelatin was spread on a metallized plastic support (comprising a micron thick layer of evaporated aluminum on polyethylencterephthalate (PET) at 40 C. using a coating knife (0.1 mm gap). The gelatin layer was then allowed to dry.

After the gelatin layer had dried, 0.02 grams of the suspension of yellow colored beads from part B was combined with 0.02 grams of the suspension of non-dyed (clear) beads from part A and diluted with 4mL of water. Fifty micro-liters of this combination were then coated onto the gelatin layer that was maintained at a temperature of 12 C. The coating was then allowed to dry in a refrigerator at 5 C.

Figure 3:
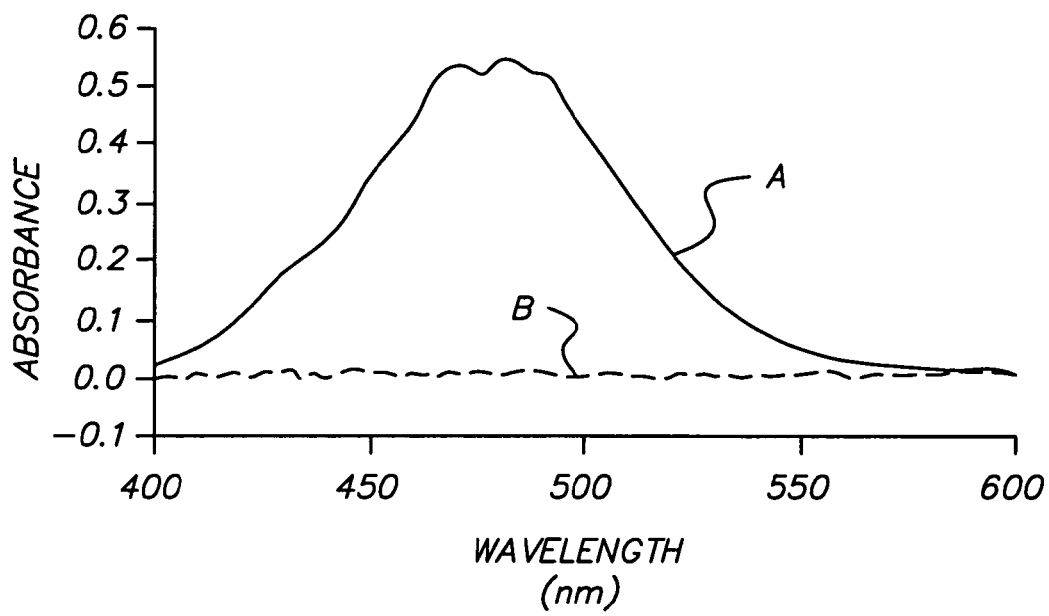
FIG. 3 is a graphical view showing the comparison of spectral response from a microsphere with no colorant, to a microsphere that is loaded with yellow dye.

FIG. 3 shows the spectral responses from colorless and yellow colored beads collected following the procedure described above, and displayed as an absorbance vs. wavelength plot. The response shows that the colorless bead has a flat response (plot B) to wavelength changes over the 400–700 nm range, consistent with the lack of any color absorbing species in the microsphere over the visible spectrum region. By contrast, the rationed intensity response (plot A) for the bead containing the yellow colorant possessed a broad peak with a maximum at about ~470 nm, with a full width at half maximum range of ~440–520 nm, consistent with a dye that has absorbed in the blue region of the visible spectrum.

Hence, this example shows that the micro-spectroscopy method described here is capable of differentiating colored from colorless microspheres.

EXAMPLE 2

This example illustrates the analysis method to detect different levels of magenta colorant in microspheres loaded with different levels of magenta colorant.

Preparation of Magenta Colored Beads M1

A suspension of magenta colored beads M1 was prepared by first dissolving 0.002 grams of Dye 2 in 0.02 grams of toluene and 5 grams of acetone. 5.0 grams of the suspension of non-dyed beads from part A of Example 1 was combined with 3 grams of acetone. This mixture was then added rapidly to 2 grams of the solution of Dye 2 in acetone and toluene while stirring to prepare a suspension of colored beads. The suspension of colored beads was then filtered using a porous cotton filter, poured into a dialysis bag (12,000 to 14,000 molecular weight cut off) and washed with distilled water for one hour. After washing, the suspension of colored beads was filtered again using a porous cotton filter.

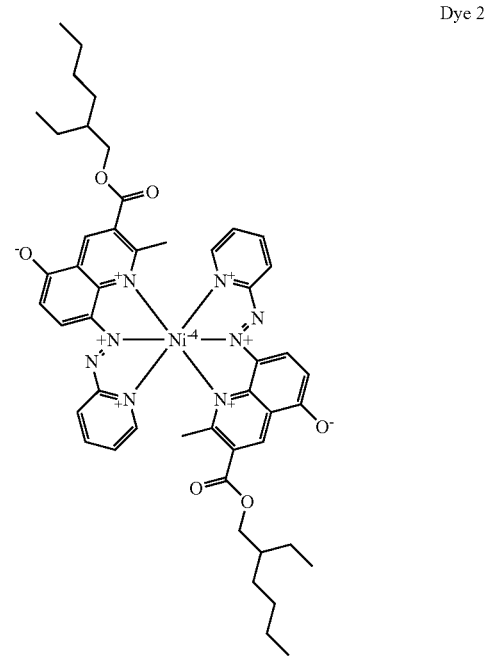

Dye 2

Preparation of Magenta Colored Beads M2

A suspension of magenta colored beads M2 was prepared by first dissolving 0.002 grams of Dye 2 in 0.02 grams of toluene and 2 grams of acetone. 5.0 grams of the suspension of non-dyed beads from part A of Example 1 was combined with 3 grams of acetone. This mixture was then added rapidly to the solution of Dye 2 in acetone and toluene while stirring to prepare a suspension of colored beads. The suspension of colored beads was then filtered using a porous cotton filter, poured into a dialysis bag (12,000 to 14,000 molecular weight cut off) and washed with distilled water for one hour. After washing, the suspension of colored beads was filtered again using a porous cotton filter.

Preparation of magenta colored beads M3

Same as preparation of magenta colored beads M2 except that the amount of dye used was 0.0015 grams instead of 0.0008 grams.

Coatings containing mixtures of beads M1, M2 and M3 with clear beads were prepared in a manner similar to that described in Example 1.

Figure 4:
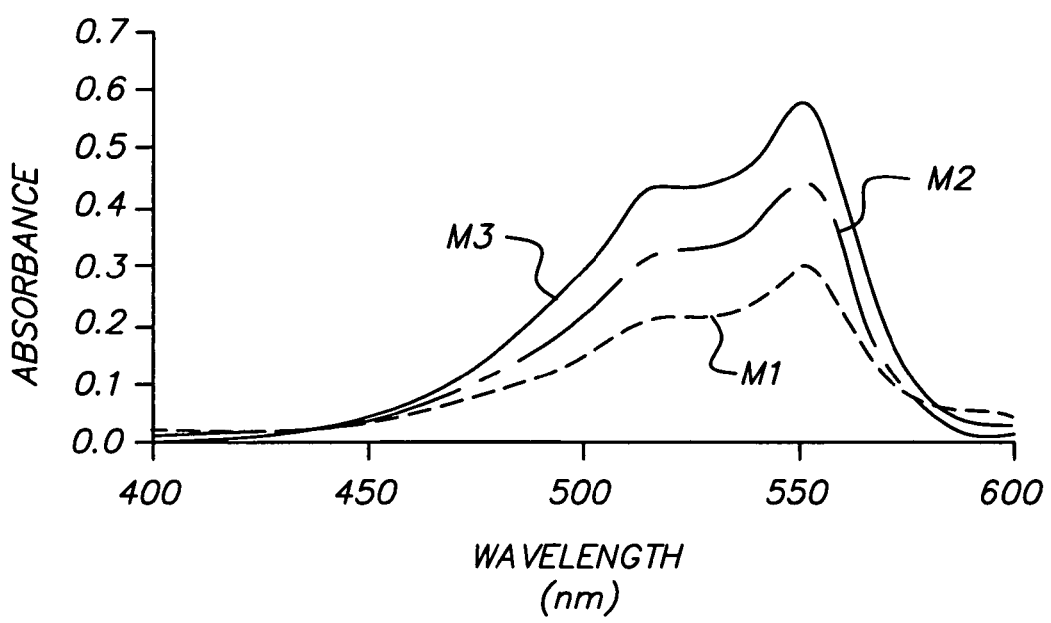
FIG. 4 is a graphical view showing a series of spectra from microspheres each containing a different level of magenta dye.

FIG. 4 shows the spectral responses from various magenta colored beads were collected following the procedure described above, and displayed as an absorbance vs. wavelength plot. The magenta beads showed a wavelength response variation with a peak at about 555 nm, and a connected shoulder at about ~520–530 nm. The full width at half maximum ranged between ~490–570 nm. This variation in spectral response over the 400–700 nm range indicates that the colorant in the bead absorbs primarily in the green region of the visible light spectrum. Three different color levels were distinctly seen in the analyzed beads, as seen by changes in the absorbance values, marked as plots M1, M2 and M3 in FIG. 4. Since the spectra were collected using apertures centered around a given bead, the data is indicative of the concentration of dye loaded in the bead, and shows that the measured concentration scales with the amount of colorant placed in the dialysis container of the dye-loading process.

Hence, this example shows that the micro-spectroscopy method described here is capable of identifying magenta colorant loaded into polystyrene beads, and also differentiate beads that contain different concentration levels of the magenta colorant.

EXAMPLE 3

This example illustrates the analysis method to detect different levels of yellow colorant in microspheres loaded with different concentrations of yellow colorant.

Preparation of Yellow Colored Beads Y1

A suspension of yellow colored beads Y1 was prepared by first dissolving 0.002 grams of Dye 1 in 0.02 grams of toluene and 2 grams of acetone. 5 grams of the suspension of non-dyed beads from part A was combined with 3 grams of acetone. This mixture was then added rapidly to the solution of Dye 1 in acetone and toluene while stirring to prepare a suspension of colored beads. The suspension of colored beads was then filtered using a porous cotton filter, poured into a dialysis bag (12,000 to 14,000 molecular weight cut off) and washed with distilled water for one hour. After washing, the suspension of colored beads was filtered again using a porous cotton filter.

Preparation of Yellow Colored Beads Y2

Same as preparation of yellow colored beads Y1 except that the amount of dye used was 0.004 grams instead of 0.002 grams.

Preparation of Yellow Colored Beads Y3

A suspension of yellow colored beads Y3 was prepared by first dissolving 0.006 grams of Dye 1 in 0.02 grams of toluene and 2 grams of acetone. 2.5 grams of the suspension of non-dyed beads from part A were combined with 3 grams of acetone. This mixture was then added rapidly to the solution of Dye 1 in acetone and toluene while stirring to prepare a suspension of colored beads. The suspension of colored beads was then filtered using a porous cotton filter, poured into a dialysis bag (12,000 to 14,000 molecular weight cut off) and washed with distilled water for one hour. After washing, the suspension of colored beads was filtered again using a porous cotton filter.

Coatings containing mixtures of beads Y1, Y2, and Y3 with clear beads were prepared in a manner similar to that described in Example 1.

Figure 5:
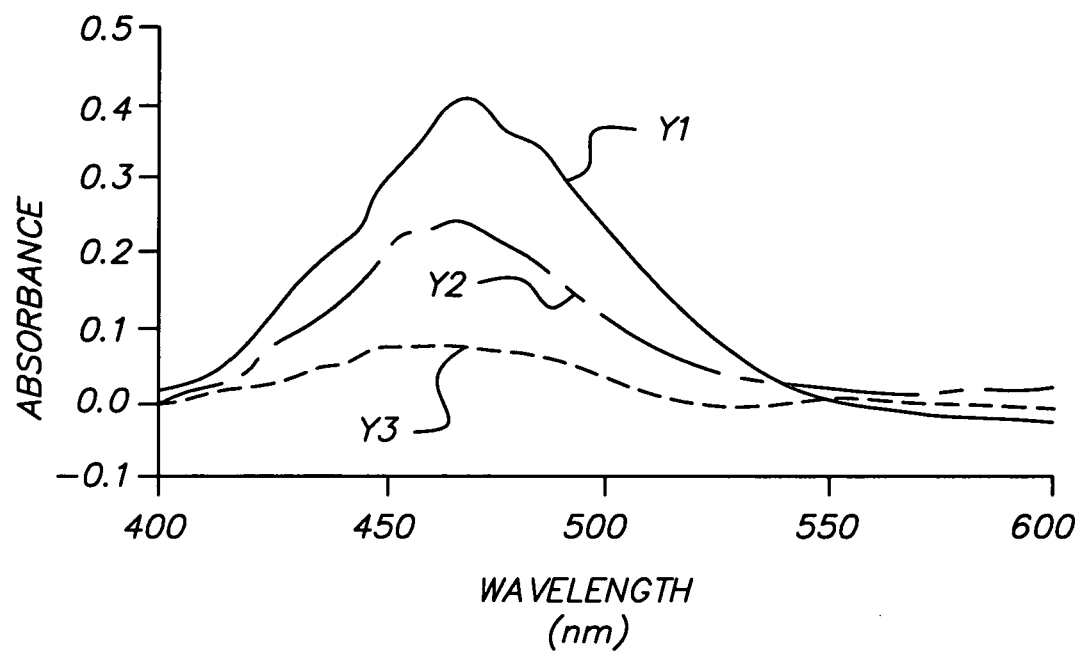
FIG. 5 is a graphical view showing a series of spectra from microspheres each containing a different level of yellow dye.

FIG. 5 shows the spectral responses from various yellow colored beads were collected following the procedure described above, and displayed as an absorbance vs. wavelength plot. The yellow beads showed a wavelength response variation with a peak at about 470 nm, with a full width at half maximum that 440–510 nm. This intensity variation in spectral response over the 400–700 nm range indicates that the colorant in the bead absorbs primarily in the blue region of the visible light spectrum. Three different color levels were distinctly seen in the analyzed beads, as seen by changes in the absorbance values of the beads, marked as plots Y1, Y2 and Y3 in FIG. 5. Since the spectra were collected using apertures centered at a given bead, the data is indicative of the concentration of dye loaded into the bead, and this appears to scale with the amount of colorant placed in the dialysis container of the dye loading process.

Hence, this example shows that the micro-spectroscopy method described here is capable of identifying the yellow colorant, and differentiate beads that contain different concentration levels of the yellow colorant.

EXAMPLE 4

This example illustrates the analysis method to detect orange colorant in microspheres loaded with a combination of magenta and yellow colorant.

Preparation of Orange Colored Beads

A suspension of orange colored beads was prepared by first dissolving 0.0015, grams of Dye 2 and 0.016 grams of Dye 1 in 0.02 grams of toluene and 2 grams of acetone. When the dyes were completely dissolved, 1 mL of the dye solution was removed. The remainder was used for loading. 2.5 grams of the suspension of non-dyed beads from part A were combined with 1.5 grams of acetone. This mixture was then added rapidly to the solution of Dye 1 and Dye 2 in acetone and toluene while stirring to prepare a suspension of colored beads. The suspension of colored beads was then filtered using a porous cotton filter, poured into a dialysis bag (12,000 to 14,000 molecular weight cut off) and washed with distilled water for one hour. After washing, the suspension of colored beads was filtered again using a porous cotton filter.

Coatings were prepared in a manner similar to that described under Example 1.

Figure 6:
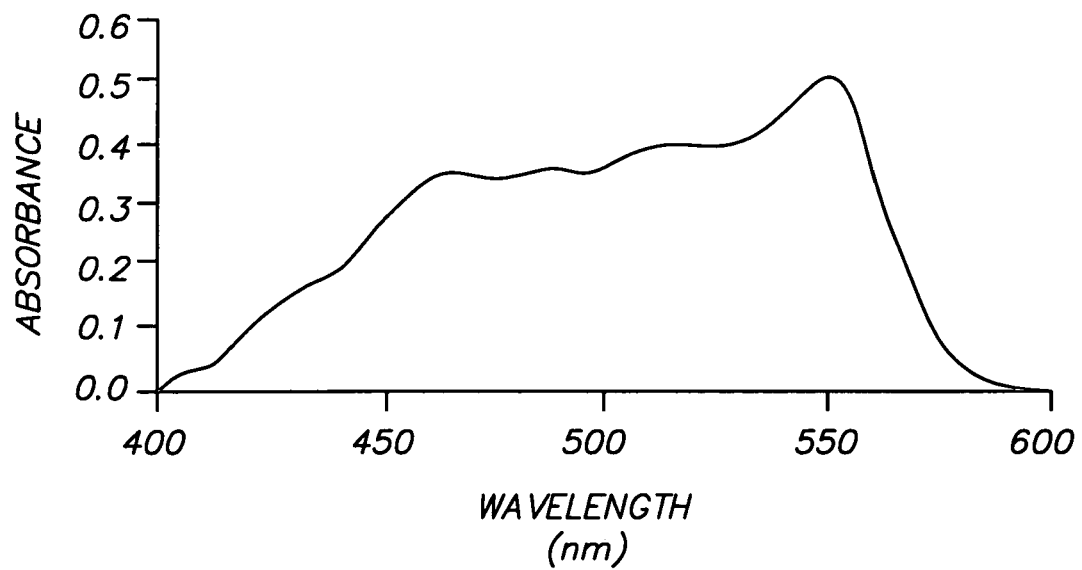
FIG. 6 is a graphical view showing the color response from microspheres containing orange dye. This response is a combination of the response from the yellow and magenta colorants.

FIG. 6 shows the spectral responses from orange colored beads were collected following the procedure described above, and displayed as an absorbance vs. wavelength plot. The orange bead showed a relatively broad wavelength response variation with a peak at about 555 nm, and a second extended shoulder with a small peak at ~470 nm. The full width at half maximum stretched from 430–570 nm. These characteristics are consistent with a colorant that absorbs primarily in the blue and green regions of the visible light spectrum.

This wide wavelength response is also consistent with the presence of both the magenta and yellow dyes in the beads. Hence, this example shows that the micro-spectroscopy method described here is capable of identifying the presence of mixed colorants (such as magenta and yellow dyes to produce orange colorant), made by loading the beads with a mixture of magenta and yellow dyes.

In each of these examples, after the color and color level of a microsphere is identified, comparison is made with known colorants to identify the unknown analyte in the sample. This can be done through the use of look-up-tables or the like in a digital processor.

The invention has been described in detail with particular reference to certain preferred embodiments thereof, but it will be understood that variations and modifications can be effected within the spirit and scope of the invention.

PARTS LIST 1 light source
2 collector lens assembly
3 exciter filter
4 dichroic mirror
5 objective lens
6 microarray specimen
7 barrier filter
8 variable zoom lens
9 removable mirror
10 digital camera
11 spectrometer aperture
12 video monitor
13 micro-spectrometer
14 angled mirror
15 mechanical shutter 20 excitation light
21 emitted light
100 microarray
101 no color microsphere
102 one color microsphere
103 colored microsphere
104 colored microsphere
105 colored microsphere
106 colored microsphere
110 substrate

What is claimed is:

1. A method of determining one or more color characteristics of a colored microsphere comprising:
    providing a microarray of microspheres, including at least one colored microsphere that has a color characteristic;
    producing a magnified optical image of individual microspheres of said microarray;
    locating an image of a microsphere at the aperture of a spectrometer to confine the color region of interest of the located microsphere in order to determine one or more color characteristics thereof; and
    determining said one or more color characteristics of said located microsphere by means of said spectrometer.

2. The method of claim 1 wherein said providing provides a microarray of randomly distributed microspheres at least one of which has a color characteristic.

3. The method of claim 1 wherein said color characteristic of said at least one microsphere is one or more of color type and color level.

4. The method of claim 1 including moving said micro array relative to said spectrometer aperture to locate a desired microsphere image in said aperture.

5. The method of claim 1 wherein at least two times the area defined by the diameter D of the microspheres image is located in said aperture of said spectometer.

6. The method of claim 1 wherein between 0.5 and two times the area defined by the diameter D of the microsphere image is located in said aperture of said spectrometer.

7. The method of claim 1 wherein less than 0.5 times the area defined by the diameter D of the microsphere image is located in said aperture of said spectrometer.

8. The method of claim 1 wherein said provided microarray of microspheres further includes a microsphere containing no colorant and wherein said one or more color characteristics of said colored microsphere are determined by comparison to said microsphere containing no colorant.

9. The method of claim 1 wherein color or colors of said colored microsphere is determined by detecting light emitted by and/or reflected from said colored microsphere over a range of wavelengths including visible and/or ultraviolet light.

10. The method of claim 9 wherein the level of said detected color or colors in said colored microsphere is determined by the measured intensity of said wavelengths of said emitted or reflected light.

11. A method of determining the color type and color intensity of a colored microsphere comprising:
    providing a microarray of randomly distributed microspheres including at least one colored microsphere having color type and color intensity characteristics and at least one microsphere containing no colorant;
    providing a spectrometer having an aperture, said spectrometer detecting light over a range of wavelengths including visible and/or ultraviolet light;
    producing a background image detected by said spectrometer when no light is emitted by or reflected from said microarray of microspheres;
    producing a reference image detected by said spectrometer by locating a magnified image of said microsphere containing no colorant in the aperture of said spectrometer after said microsphere has been illuminated to produce emitted or reflected colorless light;
    producing a sample image detected by said spectrometer by locating a magnified image of said at least one colored microsphere in the aperture of said spectrometer after said microsphere has been illuminated to produce emitted or reflected colored light; and
    detecting the color type and color intensity of said at least one colored microsphere as a function of said detected reference image, background and image and sample image.

* * * * *